United States Patent [19]

Haschke et al.

[11] 4,007,222
[45] Feb. 8, 1977

[54] PROCESS FOR THE PRODUCTION OF 2-CHLOROCAPROIC ACIDS

[75] Inventors: Heinz Haschke, Weissenstein, Austria; Wolfgang Leuchtenberger, Bruchkobel, Germany; Gerd Schreyer, Hanau, Germany; Werner Schwarze, Frankfurt, Germany

[73] Assignee: Deutsche Gold- und Silber-Scheideanstalt vormals Roessler, Frankfurt, Germany

[22] Filed: Aug. 22, 1975
[21] Appl. No.: 607,051
[30] Foreign Application Priority Data
 Aug. 22, 1974 Germany .......................... 2440213
[52] U.S. Cl. ..................... 260/518 A; 260/326 A; 260/514 J; 260/534 R; 260/534 E; 260/539 R; 260/694
[51] Int. Cl.$^2$ .......................................... C07B 9/00
[58] Field of Search ....... 260/539 R, 518 A, 534 R, 260/534 E, 534 L, 326 E, 326 A, 694, 514 J

[56] References Cited
UNITED STATES PATENTS 3,534,094  10/1970  Koenig et al. ................. 260/534 R
3,634,504  1/1972  Young .......................... 260/539 R

OTHER PUBLICATIONS

Houben–Weyl, Methoden der Organischen Chemie, vol. 5/3 (1962), pp. 623–631.
Weygand et al., Preparative Organic Chemistry, 1972, pp. 172–180.

*Primary Examiner*—Richard L. Raymond
*Attorney, Agent, or Firm*—Cushman, Darby & Cushman

[57] ABSTRACT

2-Chloro-n-caproic acid and 6-substituted 2-chloro-n-caproic acids are produced from n-caproic acid or 6-substituted n-caproic acids are chlorinated in the presence of sulfur halides and phosphorus halides at elevated temperatures using for each mole of caproic acid there is used up to about 1.2 mole of chlorine and as catalyst at least one compound of the group of sulfur chlorides, sulfur bromides, phosphorus chloride and phosphorus bromide at a temperature of about 110° to 130° C.

12 Claims, No Drawings

PROCESS FOR THE PRODUCTION OF 2-CHLOROCAPROIC ACIDS

The invention concerns a process for the production of 2-chloro-n-caproic acid or of 6-substituted 2-chloro-n-caproic acid. These compounds are especially valuable as intermediate products in the production of the aminoacid lysine.

It is known to produce the corresponding 2-chlorocarboxylic acids from saturated aliphatic carboxylic acids by the action of chlorine or chlorine yielding substances such as thionyl chloride. The reactions take place at elevated temperatures in the presence of light and in a given case in the presence of catalysts. As catalysts there are chiefly employed sulfur, phosphorus, iodine, ferric chloride, organic peroxides or halogenides, especially chlorides of sulfur and phosphorus, in a given case mixtures of these substances are used. In the reactions there are formed to a considerable extent in addition to the 2-chlorocarboxylic acids other compounds such as di and trichlorocarboxylic acids and with carboxylic acids having more than two carbon atoms there are formed mixtures of isomeric chlorocarboxylic acids. Thus in chlorination of caproic acid with 1.6 equivalents of thionyl chloride and 1 equivalent of chlorine at 100° C. or in the presence of catalytic amounts of sulfur and phosphorus pentachloride with 1,5 equivalents of chlorine at 140° C. the yield of 2-chlorocaproic acid amounts to less than 50% (Houben-Weyl, Methoden der organischen Chemie, Vol. 5/3, pages 623 to 631, especially pages 626 to 627). In fact the desired product was less than the yield of by-products.

It is also known chlorinate carboxylic acids, namely carboxylic acids with long chains, in small amounts by treatment with boiling thionyl chloride under the influence of light and to convert into the acid chloride and then to produce esters from the acid chlorides (Rodin, J. Org. Chem. Vol. 38 (1973) pages 3919 to 3921). The process is very expensive and has no significance for a chlorination on an industrial scale.

It is also known to chlorinate 6-chlorocaproic acid in aqueous, alkaline medium, i.e., by means of hypochlorite, under the influence of light at temperatures of −40° to +60° C. With this procedure the reaction goes as selectively as possible to 2,6-dichlorocaproic acid, if one is content with reaction of less than 50%, see Konig. German Auslegeschrift No. 1,234,201.

There has now been found a process for the production of 2-chloro-n-caproic acid or 6-substituted 2-chloro-n-caproic acids from n-caproic acid or 6-substituted n-caproic acids by chlorination in the presence of sulfur and phosphorus halogenides at elevated temperatures which is characterized by the use of up to about 1.2 moles of chlorine for each mole of caproic acid and as catalyst at least one compound of the group of sulfur chlorides, sulfur bromides, phosphorus chlorides and phosphorus bromides and by carrying out the reaction at temperatures of about 110° to 130° C. Surprisingly according to this process substantially higher yields of the desired 2-chlorocaproic acids are produced than by known processes.

According to the process of the invention there are especially chlorinated n-caproic acids which correspond to the general formula R—$(CH_2)_5$—COOH in which R is hydrogen, acylamino such as acetylamino and benzoylamino, phthalimido, p-toluene-sulfonamido, benzenesulfonamido, the group —NH—CO—NH—$(CH_2)_5$—COOH or the group —NH—CS—NH—$(CH_2)_5$—COOH or preferably chlorine or bromine.

The n-caproic acids can be added as such or in admixture with organic solvents. As solvents there can be used liquids which are substantially inert under the reaction conditions. There are especially employed chlorinated aliphatic and aromatic hydrocarbons such as chlorinated alkanes, e.g., methylene chloride, chloroform, carbon tetrachloride, perchloroethylene, trichloroethane, tetrachloroethane, monochlorobenzene, dichlorobenzene. Advantageously in general the caproic acids are only moderately diluted with the solvent, namely there is used not more than about 1.5 liters, especially not more than 0.5 liters of solvent per mole of caproic acid. The type and amount of solvent depends in a given case to a certain extent upon the type of caproic acid. Preferably the caproic acids are used undiluted.

The chlorination takes place according to the invention at temperatures between about 110° and 130° C., preferably at temperatures between 115° and 125° C. Advantageously there is employed intensive mixing during the chlorination.

Although the pressure can be chosen at will, it is generally suitable to use normal pressure or perhaps a slightly elevated pressure. The pressure adjusts itself in a given case according to the volatility of the materials present in the reaction mixture.

For the chlorination according to stoichiometry there is necessary to use chlorine in an amount equimolar to the caproic acid and it is suitable to add amounts which do not substantially deviate from this. Generally for each mole of caproic acid there is used up to 1.2 mole of chlorine, advantageously 0.9 to 1.1 mole of chlorine. Preferably the reaction is finished when here are reacted for each mole of caproic acid 0.98 to 1.05 mole of chlorine.

A preferred procedure is to supply the chlorine to the reaction mixture in gaseous form, especially in a homogeneous stream, namely only in the amount in which it is taken up from the reaction mixture. At what rate the chlorine can be added depends to a certain extent on the type of caproic acid and the remaining reaction conditions, as for example, according to the temperature, according to the amount of catalyst and in a given case according to the type and amount of solvent. Suitably there is added hourly about ¼ to ½ of the required total amount, the total amount consequently is added in the course of about 2 to 4 hours. In general after the addition of fairly exactly equimolar amounts of chlorine, the gas space over the reaction mixture is colored definitely yellow green. Hereby the endpoint of the chlorination can be recognized.

The reaction takes place in the presence of at least one compound of the group of sulfur chlorides, sulfur bromides, phosphorus chlorides and phosphorus bromides. These types of compounds are for example sulfur monochloride, sulfur dichloride, sulfur monobromide, sulfur dibromide, thionyl chloride, thionyl bromide, sulfonyl chloride, sulfonyl bromide, phosphorus trichloride, phosphorus pentachloride, phosphorus tribromide and phosphorus pentabromide. Thionyl chloride, phosphorus trichloride or their mixture is preferred. Generally it is suitable to use a total of 0.01 to 0.10 moles, preferably 0.02 to 0.08 mole, of the sulfur and phosphorus compounds for each mole of caproic acid.

In the cases in which a 6-substituted caproic acid is reacted, in which in the substituents a halogenation can also occur, as for example in the caproic acids substituted by acylamino (alkanoylamino), p-toluenesulfonamido, —NH—CO—NH—$(CH_2)_5$—COOH or —NH—CS—NH—$(CH_2)_5$—COOH, it is generally necessary to additionally add per mole of caproic acid 1.01 to 1.10 mole, preferably 1.02 to 1.08 mole of sulfur and/or phosphorus halide. Suitably in these cases the caproic acids are first treated with the sulfur halide or phosphorus-halide at elevated temperatures and then the chlorine is supplied.

Advantageously all materials are added in "water free" form. The water content, for example of the caproic acid, should suitably be so limited that the water at most is 50%, preferably at most 20%, of the total amount which is equivalent to the sulfur and phosphorus halides added as catalysts.

The resulting reaction mixture in many cases can be further used directly for the working up of 2-chlorocaproic acid to lysine, especially if the chlorination takes place in the absence of a solvent. To recover the pure 2-chlorocaproic acids the reaction mixture is worked up in known manner. For example, the catalyst is hydrolyzed, in a given case at elevated temperature, by the addition of water and the 2-chlorocaproic acids spearated from the byproducts, possible non-reacted portions of the caproic acids and the solvents by distillation under reduced pressure, by crystallization and especially by extraction, for example with aliphatic or aromatic hydrocarbons, or in a given case chlorinated aliphatic or aromatic hydrocarbons. It can be advantageous to first esterify the 2-chlorocaproic acid with lower alkanols, e.g., of 1 to 3 carbon atoms such as methanol, ethanol or propanol-2, then to separate this ester by distillation or extraction and subsequently to hydrolyze the ester.

The 2-chlorocaproic acids or their esters can be converted into D,L-lysine by reaction with ammonia or ammonia yielding materials such as hexamethylenetetramine, solutions of ammonia in ammonium nitrate or in ammonium thiocyanate, or with phthalimide, sodium phthalimide, potassium phthalimide, benzenesulfonamide, p-toluenesulfonamide and thiourea, and in a given case using a hydrolysis. For example, 2,6-dichlorocaproic acid is reacted with phthalimide to form the 2,6 di-phthalimide derivative of caproic acid and this reacted by hydrolysis to D,L-lysine or the 2-chloro-6-benzoyl aminocaproic acid is reacted with ammonia to 6-N-benzoyl lysine and this is reacted by hydrolysis to form D,L-lysine.

Unless otherwise indicated, all parts and percentates are by weight.

EXAMPLE 1

In a reaction vessel provided with a stirrer and which was protected against introduction of moisture there were present 116 grams (1.00 mole) of n-caproic acid and 19 grams (0.7 mole) of phosphorus tribromide. The mixture was heated to 130° C. While the mixture was held at this temperature with stirring there was introduced into the vessel from below chlorine gas in a uniform stream. The chlorine gas was dried with concentrated sulfuric acid. The chlorine flow as so regulated that inside of 60 minutes about 0.25 mole was introduced. When the gas space above the reaction mixture after 235 hours was colored yellow-green the introduction of chlorine was stopped. The reaction mixture was then cooled to room temperature. A sample of the reaction mixture showed in NMR-spectroscopy to be of a purity of 97%, *) a mixture of 90% 2-chloro-n-caproic acid and 10% 2-chloro-n-capronic acid chloride.

*) as to the content of the 2-chlorocaproic-product, especially

EXAMPLE 2

There were present in a reaction vessel according to Example 1, 151 grams (1.00 mole) of 6-chloro-n-caproic acid. The acid was melted by heating to 35° C. and then treated with 6.0 grams (0.05 mole) of thionyl chloride which was added dropwise with stirring. The mixture was heated to 120° C. and it was held at this temperature while dry chlorine gas was introduced. The gas stream was so regulated that inside 60 minutes there was added 0.32 mole of water. Since the yellow-green color developed after 187 minutes of the gas space above the reaction mixture, the chlorine introduction as broken off. The reaction mixture was cooled to room temperature, treated with 50 ml of water to hydrolyze the thionyl chloride, and after addition of 100 ml of benzene, distilled under reduced pressure. There were recovered 181 grams of 2,6-dichloro-n-caproic acid, corresponding to a yield of 98% based on the added 6-chloro-n-caproic acid. The dichlorocaproic acid had a boiling point of 115° to 120° C. at 0.4 millibar and a refractive index at $n_D^{25}$ of 1.4777. It was found to be pure by elemental analysis and NMR-spectroscopic investigation.

EXAMPLE 3

There were present in a reaction vessel according to claim 1, 235 grams of 6-benzoylamino-n-caproic acid (1.00 mole) having a melting point of 77° C. The acid was melted by heating to 80° C. and then with stirring there were added dropwise 151 grams (1.10 moles) of phosphorus trichloride. The mixture was heated to 115° C. and while the mixture was held at this temperature there was led in dry chlorine glass. The gas flow was so regulated that there was added hourly 0.33 mole of chlorine. When, after 3 hours, the gas space above the reaction mixture was colored yellow-green the introduction of chlorine was stopped. The reaction mixture was cooled to room temperature, treated with 50 ml of water to hydrolyze the phosphorus trichloride, then diluted with 500 ml of methylene chloride and extracted twice, each time with 200 ml of water. The water was driven off from the remaining organic phase by means of 150 ml of benzene under reduced pressure. There crystallized from the residue 248 grams of 2-chloro-6-benzoylamino-n-caproic acid. The acid was found by elemental analysis and NMR spectroscopic investigation to be 98%. This corresponds to a yield of 92% based on the added 6-benzoylamino-n-caproic acid.

EXAMPLE 4

The procedure was the same as in example 2 but there were added 195 grams (1.00 mole) of 6-bromo-n-caproic acid rather than 6-chloro-n-caproic acid. The reaction mixture after cooling to room temperature was treated with 100 ml of methanol. The mixture was held for 2 hours at 80° C. with stirring and then fractionally distilled under reduced pressure. There were recovered 233 grams of 2-chloro-6-bromo-n-caproic acid methyl ester. The ester was found to be at least 98% by elemental analysis and NMR spectroscopic investigation. The yield corresponded to 96% based on the 6-bromo-n-caproic acid added. The ester was hydrolyzed in the usual manner with hydrogen bromide at the boiling point to form 2-chloro-6-bromo-n-caproic acid.

The process can comprise, consist essentially of or consist of the stated steps and ingredients.

We claim:

1. A process for the production of 2-chloro-n-caproic acid or 6-substituted-2-chloro-n-caproic acid from (1) n-caproic acid or (2) 6-substituted n-caproic acid wherein the substituent is an acylamino where the acyl is the acyl of a carboxylic acid, phthalimido, p-toluenesulfonamido, benzenesulfonamido, —NH—CO—N(CH$_2$)$_5$—COOH, —NH—CS—NH—(CH$_2$)$_5$—COOH, chlorine or bromine comprising chlorinating in the presence of a sulfur chloride, sulfur bromide, phosphorus chloride or phosphorus bromide as a catalyst at 110° to 130° C., using up to 1.2 mole of chlorine per mole of (1) or (2) as the chlorinating agent.

2. The process of claim 1 wherein the catalyst consists essentially of said sulfur chloride, sulfur bromide, phosphorus chloride or phosphorus bromide.

3. A process according to claim 1 wherein the catalyst is thionyl chloride, thionyl bromide, sulfur monochloride, sulfur monobromide, sulfur dichloride, sulfur dibromide, sulfonyl chloride, sulfonyl bromide, phosphorus trichloride, phosphorus tribromide, phosphorus pentachloride or phosphorus pentabromide.

4. A process according to claim 3 wherein the acyl of a carboxylic acid is lower alkanoyl.

5. A process according to claim 3 wherein the starting material is n-caproic acid or 6-substituted n-caproic acid wherein the substituent is acetylamino, benzoylamino, phthalimido, p-toluenesulfonamido, —NH—CO—NH—(CH$_2$)$_5$—COOH, —NH—CS—NH—(CH$_2$)$_5$—COOH, Cl or Br, the catalyst is thionyl chloride, thionyl bromide, sulfur monochloride, phosphorus trichloride, phosphorus tribromide or phosphorus pentachloride and the amount of chlorine is 0.9 to 1.2 moles per mole of the caproic acid.

6. A process according to claim 5 wherein the catalyst comprises phosphorus trichloride or thionyl chloride.

7. A process according to claim 3 wherein there is employed 0.9 to 1.1 mole of chlorine per mole of the caproic acid.

8. A process according to claim 7 wherein there is used about 0.01 to 0.10 mole of the catalyst per mole of the caproic acid.

9. A process according to claim 8 wherein the chlorine is supplied in a gaseous form at an hourly rate of ¼ to ½ of the total amount required for the chlorination.

10. A process according to claim 3 wherein the compound chlorinated is n-caproic acid.

11. A process according to claim 3 wherein the compound chlorinated is 6-chloro-n-caproic acid or 6-bromo-n-caproic acid.

12. A process according to claim 3 wherein the compound chlorinated is 6-benzoylamino-n-caproic acid.

* * * * *